United States Patent [19]

Duncan

[11] 4,381,000
[45] Apr. 26, 1983

[54] DEVICE FOR USE IN HUMAN COPULATION

[76] Inventor: Lee G. Duncan, 898 N. Highland Ave., NE., Atlanta, Ga. 30306

[21] Appl. No.: 250,248

[22] Filed: Apr. 2, 1981

[51] Int. Cl.³ .............................................. A61F 5/00
[52] U.S. Cl. ..................................................... 128/79
[58] Field of Search ......................... 128/79, 132, 294

[56] References Cited

U.S. PATENT DOCUMENTS

| | | | |
|---|---|---|---|
| 1,511,572 | 10/1924 | Marshall | 128/79 |
| 2,705,951 | 4/1955 | Crowner | 128/79 X |
| 4,022,196 | 5/1977 | Clinton | 128/79 |
| 4,194,502 | 3/1980 | Eckels | 128/79 |

FOREIGN PATENT DOCUMENTS

| | | | |
|---|---|---|---|
| 260938 | 6/1913 | Fed. Rep. of Germany | 128/79 |
| 875853 | 5/1953 | Fed. Rep. of Germany | 128/79 |
| 2355495 | 2/1978 | France | 128/79 |
| 23165 | of 1900 | United Kingdom | 128/79 |

*Primary Examiner*—Dalton L. Truluck
*Attorney, Agent, or Firm*—Luke J. Wilburn, Jr.; Wellington M. Manning, Jr.

[57] ABSTRACT

A device to be worn by the human male during sexual intercourse to support the penis and delay ejaculation during the act of copulation, comprising a semi-rigid sheath which encircles the shaft of the penis from the base to a point just behind the glans to shield the same from contact with the vagina of the female, and a support harness to be worn about the lower body of the male and support the sheath to prevent its longitudinal movement along the shaft of the penis during copulation. The harness includes an elongate semi-rigid section having a base portion which is located centrally on the lower abdomen of the male above the penis to firmly engage the pubic bone, and a semi-rigid member which extends from the base portion through the crotch area of the wearer and has a terminal end portion which firmly engages the lower vertebra of the spine to form a dimensionally stable support for the penis-encircling sheath. Strap means are provided for securing the semi-rigid support section of the harness to the body of the wearer.

12 Claims, 8 Drawing Figures

DEVICE FOR USE IN HUMAN COPULATION

The present invention is directed to a device to be worn by the human male during sexual intercourse to support the penis and to delay ejaculation during the act of copulation.

BACKGROUND OF THE INVENTION

Numerous devices are described in the patented literature for use by the male as an aid in the act of sexual intercourse. Such devices generally comprise penis-encircling members for restricting blood flow to the penis to maintain an erection, or prosthetic type devices to support the penis while allowing direct or partial contact thereof with the vagina of the female during the sex act.

In particular, U.S. Pat. Nos. 1,216,099; 1,511,572; 2,264,934; 3,633,572; and 4,022,196 disclose penis-supporting or encircling devices having a strap or band for attaching the device to the body of the wearer to support the same.

U.S. Pat. Nos. 938,808; 3,155,096; 3,401,687; 3,773,040; and 3,939,827 disclose devices for attachment to the penis to restict blood flow thereto or therefrom, or support the same as an assistant in the act of sexual intercourse.

U.S. Pat. Nos. 622,333 and 3,147,486 disclose devices for encircling the male penis for use in other than acts of sexual intercourse.

The sexual aid devices disclosed in the aforementioned patents are generally directed to the problem of impotence, or the inability of the human male to consumate the sex act, and are designed as an aid to alleviate such condition by supporting the male organ or by restricting flow of the blood thereto or therefrom to effect an erection.

In distinction to the aforesaid problem, there is also, at times or in certain males, a problem of premature ejaculation in performance of the sex act. Consummation of the act of sexual intercourse in the human male by ejaculation generally involves a physical stimulation of the male organ by relative movement of the skin of the penis along the shaft during the sex act, and time required for ejaculation may be influenced by physical condition and the particular emotional state of mind of the male. In certain instances, or with particular individuals, the emotional state of the male partner may be such that little if any physical stimulation of the penis is required to cause ejaculation during sexual intercourse. In such situations, premature ejaculation by the male can result in incomplete fulfillment for both the male and female partners in the act of copulation.

OBJECTS OF THE PRESENT INVENTION

It is therefore an object of the present invention to provide a device to be worn by the human male during the act of sexual intercourse which prevents premature ejaculation while supporting the penis during the act of copulation.

It is another object to provide a device for assistance in the act of sexual intercourse wherein the male penis is partially shielded by semi-rigid sheath means which is supported by a body-encircling harness during the sexual act to prevent its longitudinal movement along the shaft of the penis, thereby reducing stimulation of the penis by maintaining the skin of the shaft in a fixed position during the sexual act and reducing the chances of premature, or early, ejaculation.

It is a further object to provide a device for assistance of the male in the act of sexual intercourse whereby a penis-encircling sheath which protects the penis against overstimulation may be positively maintained at a fixed position along the length of the penis relative to the body of the male during the act of copulation.

It is still another object of the invention to provide a device for the assistance of the human male during acts of sexual intercourse which holds the skin of the shaft of the penis from relative movement therealong during the sexual act, and which device may be worn with nominal inconvenience and discomfort to the users.

SUMMARY OF THE INVENTION

Briefly, the present invention comprises a body-encircling harness and penis-encircling sheath device to be worn by the human male during the act of sexual intercourse to support the shaft of the penis behind the glans and restrict movement of the skin of the same, thereby reducing stimulation of the penis and the chance of premature ejaculation by the male during the act of sexual intercourse. The device includes a semi-rigid, elongate sheath which encircles the shaft of the penis and extends from behind the glans to the base of the same to hold and shield the skin against movement, and body-encircling harness means which supports the sheath in such a way as to prevent its movement along the shaft of the penis, relative to the body of the wearer, during movement of the male in the act of copulation.

More particularly, the harness means comprises a sheath-supporting section of relatively rigid material having a base portion to which the sheath is attached, which base portion is located on the central lower abdomen of the body of the male with a thickened upper control portion in firm engagement with the pubic bone, and a semi-rigid elongate member which extends from the base portion between the legs of the male to terminate adjacent the lower vertebra of the spinal column of the body. Flexible strap means of the harness interconnect the base portion and end of the semi-rigid elongate member and are tightened about the lower body of the wearer to firmly secure and positively position the sheath-supporting section against relative movement on the body. The sheath-supporting section of the harness means is firmly anchored at both the front and back portions of the body, i.e., against the pubic bone and against the lower vertebra of the spine, to thereby preclude longitudinal movement of the protective sheath on the shaft of the penis and reduce stimulation of the same thereby.

DETAILED DESCRIPTION OF PREFERRED EMBODIMENTS

Figure 1:
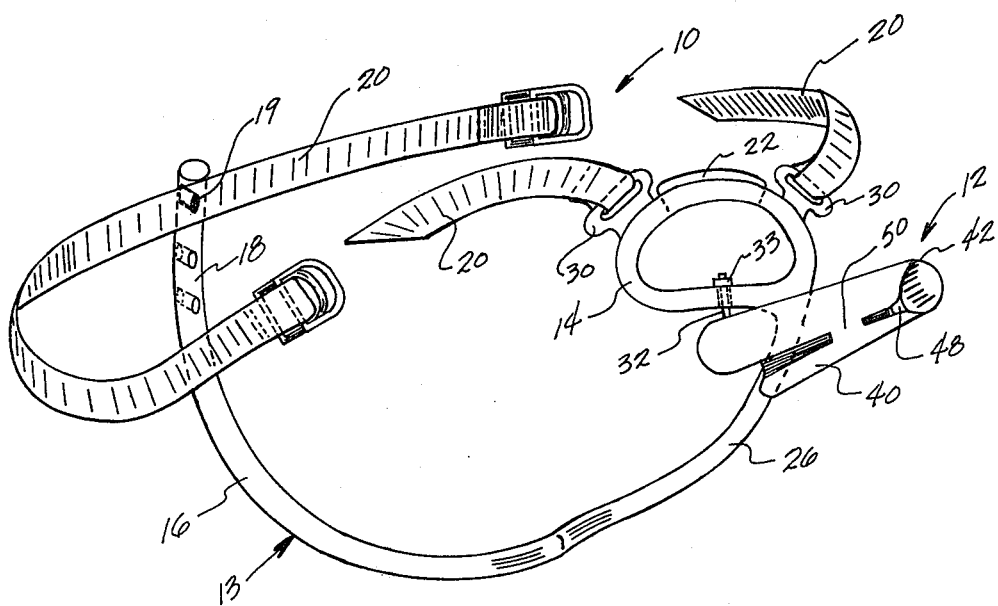
FIG. 1 is a side perspective view of the device of the present invention.
Figure 2:
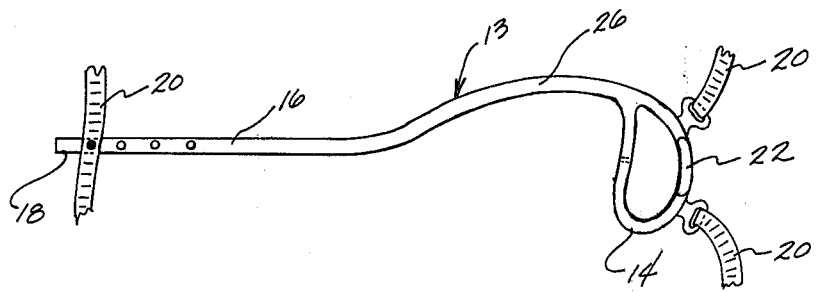
FIG. 2 is a top view, on somewhat reduced scale, of the sheath-supporting section of the harness means of the device of FIG. 1, with the elongated semi-rigid member of the section shown in somewhat less arcuately bent configuration than is seen in FIG. 1.

As seen in FIGS. 1 and 2, the sexual aid device of the present invention comprises harness means, generally indicated at 10, which is adapted to be attached to the body of the human male during the act of sexual intercourse, and sheath means 12 supported thereby for encircling the shaft of the male organ to shield and hold the skin of the shaft against relative movement along the shaft during the sex act.

As best seen in FIGS. 1 and 2, harness means 10 comprises a relatively rigid sheath-supporting section 13 having a base portion 14 of somewhat triangular, or oval, shape, and a semi-rigid, bendable elongate member 16 attached to and extending from a lower side edge of the base portion. Suitably attached to base portion 14 and to the distal end portion 18 of semi-rigid member 16 are flexible straps 20 for securing the harness means to the body of the male during use, as will be explained.

Figure 3:
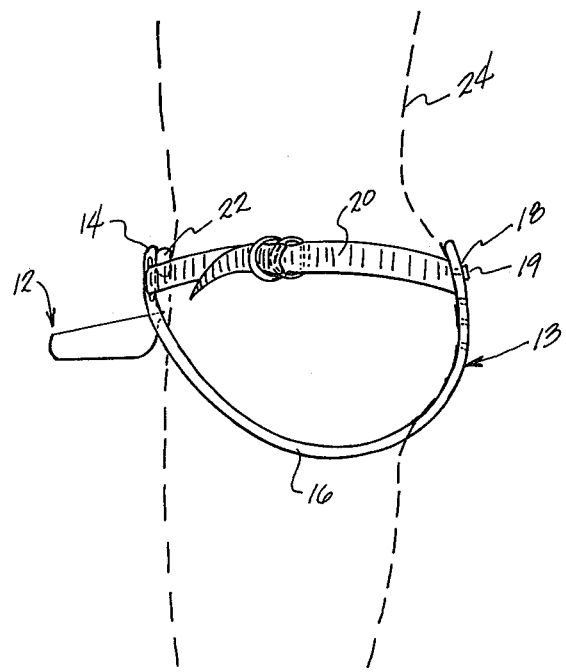
FIG. 3 is a left side view of the device of the present invention in its normal position of attachment for use on the lower body portion of a human male.
Figure 4:
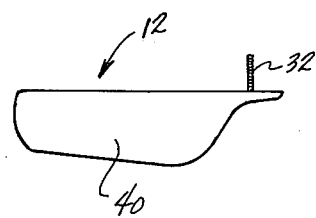
FIG. 4 is an enlarged side view of the penis-encircling sheath of the device seen in FIG. 3.

The base portion 14 of harness means 10 is of generally rigid construction and, as illustrated in FIG. 3, is positioned on the front central lower portion of the body of the male, just above the penis. The upper central portion 22 of base portion 14 at the apex of its generally triangular shape is of increased thickness and is located in juxtaposition to the pubic bone of the body to firmly, but comfortably, reside at and be retained against the pubic bone during use of the device. As illustrated in FIG. 3, semi-rigid member 16 of section 13 extends rearwardly through the crotch of the wearer and its distal end portion 18 is located adjacent the lowermost bone, or vertebra, of the spinal column. End portion 18 is maintained in firm engagement with the lower vertebra by tightening of the straps 20 about the hips of the body. FIG. 3 illustrates the approximate position of the device on the lower portion of a male body, shown in dashed lines 24.

As illustrated in FIGS. 1 and 2, elongate semi-rigid member 16 of section 13 extends from a lower side edge of base 14, and has a permanently curved portion 26 which is designed to pass the member to one side of the male penis and scrotum, after which member 16 straightens as it bends upwardly to terminate centrally of the body in overlying relation to the lower portion of the spinal cord.

Section 13 of the harness is constructed of a suitable semi-rigid, resiliently bendable material so that the same forms a relatively dimensionally stable U-shaped element of the harness. Preferably, the base portion 14 and elongate member 16 are unitarily constructed of an elongate metal rod, which may be plastic or rubber coated to provide a smooth outer surface for the same. Section 13 may also be formed of a molded synthetic plastic, or the like, shaped or formable into a semi-rigid U-shape, as illustrated in FIG. 3, when the supporting straps 20 are interconnected and tightened about the hips of the male body.

As illustrated in FIGS. 1-3, the distal end portion 18 of elongate member 16 is provided with a plurality of spaced openings to permit adjustable positioning of straps 20 which are attached thereto by fastening means 19, such as a countersunk screw or nut and bolt. The straps 20 are adjusted to accommodate the size of the male body and thus ensure firm engagement of the distal end portion 18 with the lower bone or vertebra of the spinal column. As seen in FIGS. 1 and 2, the straps 20 attached to eyelets 30 of the base portion 14 are located on opposite sides of the thickened center portion 22 of the base.

The penis-encircling sheath means 12 of the present invention is supportably attached to the lower edge of base portion 14 of section 13 by suitable means, such as a threaded bolt 32 which extends through openings in the sheath means and base portion 14 to be secured by a nut 33. As seen in FIGS. 1 and 3-5, sheath means 12, in one embodiment, comprises a semi-rigid elongate tubular body 40 defining a passageway therethrough for receiving the shaft of the penis. The glans, or head, of the penis extends beyond the outer end of the passageway, and the inner end of the body passageway is located adjacent the base of the penis, just below the base portion 14 of the harness. FIGS. 1 and 3-5 illustrate a preferred form of sheath means of the present invention wherein the elongate semi-rigid body 40 is composed of a molded soft plastic or rubber material of generally smooth surface configuration which encircles the shaft of the penis and has a tapered outer end 42 which is located directly behind the glans of the penis to facilitate smooth insertion of the device into the vagina of the female during use.

Figure 5:
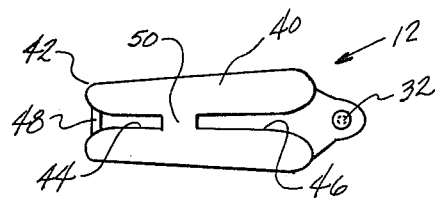
FIG. 5 is a bottom plan view of the sheath of FIG. 4.

As seen in FIG. 5, the underside of the penis encircling body 40 is provided with longitudinal slits 44, 46 which narrow inwardly from opposite ends of the body to facilitate insertion of the penis into the sheath preparatory to use of the device. Opposed edges of the body 40 along the slits 44, 46 are interconnected by elastic web portions 48, 50 located adjacent the outer end and the mid-portion of the body 40. Such elastic web portions ensure retention of the sheath on the penis during use and close securement of the outer end of the sheath about the shaft of the penis at a point directly behind the glans. Elastic web portion 48 not only facilitates insertion of the head of the penis outwardly of the sheath, but serves the important function of retracting and retaining the skin of the penis within the sheath behind the head of the penis during intercourse.

Figure 6:
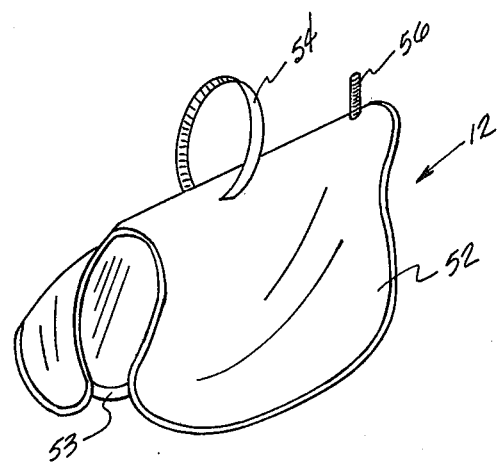
FIG. 6 is a perspective view of a modified form of sheath of the device of the present invention.
Figure 7:
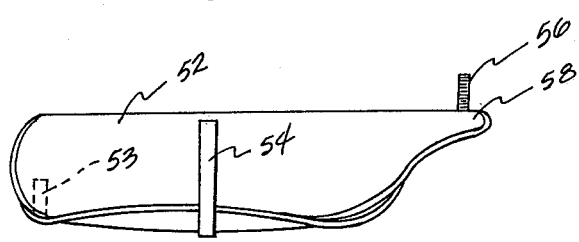
FIG. 7 is a side view of the sheath of FIG. 6, illustrating the tubular disposition of the sheath as it is employed during use.
Figure 8:
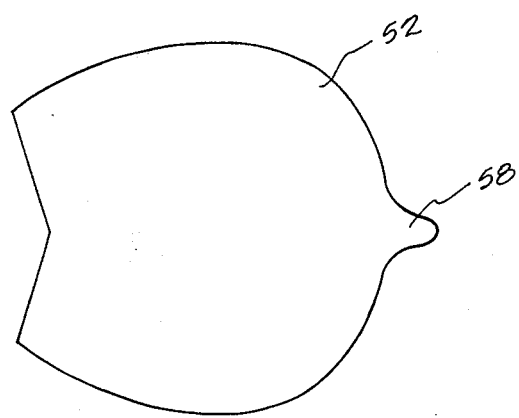
FIG. 8 is a plan view of the sheath of FIGS. 6 and 7, in open or flat condition to illustrate more clearly the geometric shape of the sheath.

FIGS. 6-8 illustrate a modified form of penis-encircling sheath means of the present invention which comprises a somewhat circularly shaped sheet 52 of semi-rigid mateial, such as plastic or leather, having a smooth surface and an overall shape, in flattened or unrolled condition as illustrated in FIG. 8. FIG. 6 illustrates the general geometric configuration of the sheet 52 when receiving the shaft of the penis. The head of the penis is inserted outwardly through the opening formed by the fold of the sheet and an interconnecting elastic strip or web 53 of material. The lower side edges of the sheet, as seen in FIG. 6, are then overlapped beneath the shaft of the penis to enclose the same, and are held in such position, as illustrated in FIG. 7, by a thin elastic band 54 attached to the sheet. In securing the sheath about the shaft of the penis, elastic band 54 is brought over the head of the penis and under the sheet to the position shown in FIG. 7. Thus the sheet 52 completely surrounds the shaft of the penis and elastic strip 53 holds the skin of the penis in a retracted position leaving the glans exposed during sexual intercourse. Fastening means, illustrated as a threaded bolt 56 located on an extended tip portion 58 of the sheet, is received within the opening in the base portion 14 of the harness means and supportably secured thereto by a nut to prevent longitudinal movement of the tubular formed sheet 52 relative to the base portion 14 during male body movement in the act of intercourse.

As can be appreciated from the foregoing detailed description of preferred embodiments of the present invention, harness means 10 is constructed in such a way that the upper control portion 22 of base portion 14 and the distal end portion 18 of the elongate member 16 are firmly held against displacement from the pubic bone and lower vertebra of the spinal column of the wearer, respectively. The semi-rigid interconnection of the same through the crotch portion of the body prevents any forward or rearward movement of the sheath means 12 along the shaft of the penis relative to the body of the male during act of copulation. Firm securement of the straps 20 of the harness likewise prevents any sideways or lateral movement of the sheath supporting section 13. The semi-rigid construction of the sheath and its elastic web portions hold the skin of the penis retracted and shielded from relative movement along the shaft by the walls of the vagina during the sex act, while permitting stimulation of the exposed glans of the penis which extends from the outer end of the sheath.

It can be appreciated that the size and dimensions of the device of the present invention may be varied to accommodate the size and anatomy of the male user. The protective sheath of the device may be manufactured in several lengths to accommodate the normal anatomical variances and ensure proper support and positioning of the penis therein.

That which is claimed is:

1. A device to be worn by the human male during the act of sexual intercourse comprising sheath means for encircling and shielding the shaft of the penis from a point directly behind the glans to the base portion thereof to retract and retain the skin of the shaft therewithin, and harness means adapted to be worn about the lower portion of the male body for supportably positioning said sheath means to prevent its longitudinal movement along the penis and relative movement of the skin along the shaft of the penis during intercourse, said harness means comprising an elongate relatively rigid section having a base portion at one end thereof for location on the central lower abdomen of the body of the male above the penis and in juxtaposition to the pubic bone, and a semi-rigid flexible elongate member attached to and extending from said base portion passing between the legs of the male body and having an end portion to be positioned adjacent the lower vertebra of the spinal column of the body, and flexible strap means for interconnecting said base portion and said end portion of said semi-rigid elongate member about the hips of the body to draw the base portion and the end portion of the elongate member into firm engagement with the pubic bone and lower vertebra of the spine of the male body, respectively.

2. A device as defined in claim 1 wherein said sheath means comprises a generally tubular shaped body of semi-rigid material, and longitudinal slits tapering inwardly from opposite ends of said body to facilitate insertion of the penis therethrough and location of the glans of the penis beyond the outer end of said body.

3. A device as defined in claim 2 wherein side edges of said body defining said slit at the outer end of said body from which the glans of the penis protrudes are interconnected by elastic means to closely contain the shaft of the penis directly behind the glans thereof and retain the skin of the shaft within said body.

4. A device as defined in claim 1 wherein said semi-rigid elongate member of said section comprises a manually bendable metal rod.

5. Apparatus as defined in claim 4 wherein said rod includes an outer plastic or rubber coating of relatively smooth surface configuration.

6. A device as defined in claim 1 wherein said base portion of said section is of generally flat triangular shape and has a thickened portion adjacent its apex for engagement with the abdomen adjacent the pubic bone to facilitate the fixed position of the base portion thereat.

7. A device as defined in claim 6 wherein said strap means include two straps connected to said base portion on opposite sides of said apex.

8. A device as defined in claim 1 including means supportably attaching said sheath means to said base portion whereby said sheath means is maintained in longitudinally fixed position relative to said base portion during intercourse.

9. A device as defined in claim 1 wherein said elongate member has a curved portion therein adjacent said base portion to permit the same to pass through the crotch area of the wearer to one side of the penis and scrotum and thereafter centrally of the crotch area to its end portion.

10. A device as defined in claim 1 wherein said sheath means comprises a semi-rigid flexible sheet of material having smooth outer surfaces and being of sufficient dimensions to extend from the base portion of the shaft of the penis to a point immediately behind the glans of the penis, and having side portions of sufficient length to overlap and fully encircle the shaft of the penis when the sheet is placed thereabout, elastic means interconnecting side edge portions of said sheet of material adjacent the glans of the penis, and elastic means for surrounding the sheet when it is wrapped in overlapping relation about the shaft of the penis.

11. A device as defined in claim 10 wherein said sheet means includes a protruding portion having means thereon for attachment of the sheet to said base portion of the harness means.

12. A device as defined in claim 1 wherein said end portion of said semi-rigid elongate member of said harness means includes means for adjustably positioning said flexible strap means therealong to accommodate the size of the body of the wearer.

* * * * *